(12) United States Patent
Gaffney et al.

(10) Patent No.: US 12,256,956 B2
(45) Date of Patent: Mar. 25, 2025

(54) METHODS FOR COUPLING DEVICE COMPONENTS AND RELATED DEVICES HAVING SUCH COMPONENTS

(71) Applicant: Boston Scientific Scimed, Inc., Maple Grove, MN (US)

(72) Inventors: Brian Gaffney, Rutland, MA (US); Paul Smith, Smithfield, RI (US); James J. Scutti, Norwell, MA (US); Rachel Marie Williams, Peoria, AZ (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 18/504,409

(22) Filed: Nov. 8, 2023

(65) Prior Publication Data
US 2024/0065722 A1   Feb. 29, 2024

Related U.S. Application Data

(63) Continuation of application No. 17/196,433, filed on Mar. 9, 2021, now Pat. No. 11,844,492.

(Continued)

(51) Int. Cl.
*A61B 17/3205* (2006.01)
*A61B 17/32* (2006.01)
(Continued)

(52) U.S. Cl.
CPC ............ *A61B 17/32056* (2013.01); *A61B 17/320016* (2013.01); *B21F 15/06* (2013.01);
(Continued)

(58) Field of Classification Search
CPC ...... A61B 17/32056; A61B 17/320016; A61B 2017/00477; A61B 2017/00867; B21F 15/06
See application file for complete search history.

(56) References Cited

U.S. PATENT DOCUMENTS 5,792,075 A   8/1998  Schwager
7,347,868 B2  3/2008  Burnett et al.
(Continued)

FOREIGN PATENT DOCUMENTS

JP   2018015064 A   2/2018
WO   2006039216 A2  4/2006

OTHER PUBLICATIONS

International Preliminary Report on Patentability and Written Opinion issued in International Application PCT/US2021/021501 on Mar. 9, 2021 (9 pages).

*Primary Examiner* — Julian W Woo
(74) *Attorney, Agent, or Firm* — Bookoff McAndrews, PLLC (57) ABSTRACT

A method for coupling a first medical device component to a second medical device component comprising altering the first medical device component from a natural state to an altered state, by reducing a cross-sectional dimension of the first medical device, fitting a first portion of the first medical device component in the altered state into a first opening of the second medical device component, wherein the first medical device component includes second portions not within the first opening of the second medical device component, and allowing the second portions of the first medical device component to revert back to the natural state.

15 Claims, 5 Drawing Sheets

Related U.S. Application Data (60) Provisional application No. 62/987,604, filed on Mar. 10, 2020.

(51) Int. Cl.
*B21F 15/06* (2006.01)
*A61B 17/00* (2006.01)

(52) U.S. Cl.
CPC .............. *A61B 2017/00477* (2013.01); *A61B 2017/00526* (2013.01); *Y10T 29/49* (2015.01)

(56) References Cited

U.S. PATENT DOCUMENTS

| | | |
|---|---|---|
| 9,700,244 B2 | 7/2017 | Laramy et al. |
| 9,801,740 B1 | 10/2017 | Thapliyal |
| 10,182,840 B2 * | 1/2019 | Raybin ............. A61B 17/32056 |
| 10,463,358 B2 * | 11/2019 | Gilmore ................ A61F 2/2478 |
| 2006/0100544 A1 | 5/2006 | Ayala et al. |
| 2011/0276091 A1 | 11/2011 | Melanson et al. |
| 2014/0100646 A1 | 4/2014 | Hassan et al. |
| 2019/0285205 A1 | 9/2019 | Broadley et al. |

\* cited by examiner

METHODS FOR COUPLING DEVICE COMPONENTS AND RELATED DEVICES HAVING SUCH COMPONENTS

CROSS-REFERENCE TO RELATED APPLICATIONS

This application is a continuation of U.S. application Ser. No. 17/196,433, filed on Mar. 9, 2021, which claims the benefit of priority from U.S. Provisional Application No. 62/987,604, filed on Mar. 10, 2020, each of which is incorporated by reference herein in its entirety.

TECHNICAL FIELD

This disclosure relates to coupling one device component to another device component. Examples of the disclosure relate to a method for coupling a nitinol wire to another component, of a dissimilar material, of a medical device, e.g., a therapeutic or diagnostic instrument. Other examples of the disclosure relate to apparatuses or medical devices including components coupled via the described method.

BACKGROUND

Nitinol has super-elastic properties that give it high flexibility, shape recoverability, kink resistance, high fatigue strength, corrosion resistance, and heat resistance. Thus, nitinol is an ideal material for medical devices and instruments, particularly in wire form. Medical devices including nitinol parts may be assembled via adhesive bonding, welding, crimping, and/or swaging the nitinol part to another component of the medical device. However, these methods may be difficult due to the hard oxide outer layer of nitinol, which limits bonding/coupling during and after the joining process. Filler material may be needed to weld or solder nitinol to stainless steel, which typically creates a weak point in the bond. This may also deteriorate the thermal properties of nitinol, which give nitinol its shape recovery characteristics.

SUMMARY OF THE DISCLOSURE

According to an example, a method for coupling a first medical device component to a second medical device component may comprise altering the first medical device component from a natural state to an altered state, by reducing a cross-sectional dimension of the first medical device, fitting a first portion of the first medical device component in the altered state into a first opening of the second medical device component, wherein the first medical device component includes second portions not within the first opening of the second medical device component, and allowing the second portions of the first medical device component to revert back to the natural state.

In another example, the method may further comprise, after the fitting step, allowing the cross-sectional dimension of the first portion of the first medical device component to increase to a dimension of the opening.

In another example, the altering step may include applying a force to the medical device component in a direction transverse to the direction of the cross-sectional dimension, and wherein the allowing step includes removing the force. In the natural state, the first medical device component may be dimensionally constrained from entering the first opening. The first medical device component may be a wire. The wire may comprise nitinol. The altering step may include stretching the wire so that a diameter of the wire is less than or equal to a width of the first opening. The second medical device component may be disk-shaped, and the first opening may include a slot extending from an outer edge of the second medical device component to a point radially inward of the outer edge.

In another example, the first medical device component may be a wire, and the fitting step may include sliding the second medical device component over the wire via the slot. The second medical device component may include a second opening, and the method may further include fitting a third portion of the first medical device component in the altered state into the second opening.

In another example, the method may further include fitting a third portion of the first medical device component into the first opening of the second medical device component.

In another example, the first medical device component may be coupled to the second medical device component so that first medical device component is not rotatable relative to the second medical device component. The first medical device component may be an actuation element for actuating an end effector of a medical device. A single wire may comprise the actuation element and the end effector, and the end effector may comprise a snare loop. The single wire may comprise nitinol, and two portions of the single wire may be fitted within the second medical device component.

According to another example, a medical device may comprise a nitinol wire defining a loop, a first strand, and a second strand, each of the first strand and the second strand extending proximal to the loop, and a receiving component coupled to the first strand and the second strand, wherein the receiving component includes a first opening, and a portion of the first strand extends through the first opening, wherein a diameter of the portion of the first strand is less than a diameter of a remaining portion of the first strand. A portion of the second strand may extend through the first opening, wherein a diameter of the portion of the second strand is less than a diameter of a remaining portion of the second strand. The receiving component may further include a second opening, and a portion of the second strand extends through the second opening, wherein a diameter of the portion of the second strand is less than a diameter of a remaining portion of the second strand. A diameter of the portion of the first strand may be less than a diameter of a portion of the nitinol wire defining the loop.

According to another example, a medical device may comprise a shaft, a handle connected to a proximal portion of the shaft, a nitinol wire extending from the handle to the shaft, and a receiving component, wherein the receiving component is positioned within the handle or the shaft, wherein a portion of the nitinol wire extends through the receiving component, and a diameter of the portion of the nitinol wire is less than a diameter of a remaining portion of the nitinol wire.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

DETAILED DESCRIPTION

Reference will now be made in detail to aspects of the disclosure, examples of which are illustrated in the accompanying drawings. Wherever possible, the same or similar reference numbers will be used through the drawings to refer to the same or like parts. The term "distal" refers to a portion farthest away from a user when introducing a device into a subject (e.g., patient). By contrast, the term "proximal" refers to a portion closest to the user when placing the device into the subject.

Both the foregoing general description and the following detailed description are exemplary and explanatory only and are not restrictive of the features, as claimed. As used herein, the terms "comprises," "comprising," "having," "including," or other variations thereof, are intended to cover a non-exclusive inclusion such that a process, method, article, or apparatus that comprises a list of elements does not include only those elements, but may include other elements not expressly listed or inherent to such a process, method, article, or apparatus. In this disclosure, relative terms, such as, for example, "about," "substantially," "generally," and "approximately," are used to indicate a possible variation of ±10% in a stated value or characteristic.

Aspects of this disclosure may solve one or more of the limitations of in the art. The scope of the disclosure, however, is defined by the attached claims and not the ability to solve a specific problem. The disclosure is drawn to a method for coupling a device component to other components, and medical devices/apparatuses including components coupled via the method, among other aspects. In exemplary embodiments, one of the device components is a wire, e.g. a wire comprising nitinol, a nickel-titanium alloy having superelastic properties. This disclosure, however, is not limited to wires comprising nitinol. Device components, e.g. wires, suitable for use in methods and devices of this disclosure may comprise any material capable of stretching/elongating upon application of a force, and returning to its original, unstretched configuration upon removal of the force. Throughout this disclosure, embodiments may refer to wires comprised of nitinol. It is to be understood, however, that any materials mentioned herein and other suitable materials may be used in the methods and devices according to embodiments of the invention.

Also in exemplary embodiments described herein, the component that is altered to couple to other device components is a wire. Other components capable of elongation in one direction and shortening in another direction may be used in the devices and methods according to embodiments of the invention.

According to exemplary embodiments, a nitinol component may be altered and coupled to other materials and components via receivers. Thus, in the methods described in further detail below, a nitinol component may be coupled to other materials without using a filler or adhesives, or implementing heat exposure. Such receivers may be implemented in various medical devices or apparatuses that include nitinol, e.g., endoscopes, instruments having end effectors, etc.

Referring to FIGS. 1A-2D, an example of a method for coupling/fixing a nitinol wire 100 to a receiver 200 is further discussed below. Nitinol wire 100 has a diameter D. Diameter D is not particularly limited, and may be in the range of approximately 0.02" to 0.04", for example, approximately 0.029". Nitinol wire 100 has a circular cross-section, but is not particularly limited thereto. Diameter D is greater than width W of opening 210 of receiver 200. Receiver 200 is disk-like in shape, and may be of any suitable material, e.g., stainless steel. The receiver 200 may be formed of a material dissimilar from the wire 100. Opening 210 leads to a slot 215 having a width W throughout its length. Width W should be less than diameter D of wire 100, but is not particularly limited, and may be, for example, approximately 0.028". Slot 215 extends from the outer surface to end point 220, which may be at or about a center point of disk-shaped receiver 200. End point 220 may be shaped accordingly to accommodate for the cross-sectional shape of nitinol wire 100. However, nitinol wire 100, in an unaltered state with no force applied thereto, does not fit into receiver 200, as shown by the dotted outline representing a circumference of wire 100 in FIG. 1B.

To couple nitinol wire 100 to receiver 200, nitinol wire 100 may be altered via any suitable manner to fit into opening 210 and slot 215 of receiver 200. For example, nitinol wire 100 may be stretched, thereby forming a thinned nitinol wire 100' having a diameter D', shown in FIG. 2A. The degree by which nitinol wire 100 is thinned to nitinol wire 100' is not particularly limited, so long as nitinol wire 100' has a diameter D' that is equal to or less than width W of opening 210 of receiver 200. For example, diameter D' may be in the range of approximately 0.02" to 0.04", for example approximately 0.028", thereby equaling width W, or less than 0.028". Furthermore, nitinol wire 100 may be altered/stretched by any suitable manner. For example, one end or both ends of nitinol wire 100 may be secured in a hydraulic press or any other suitable pulling fixture. The hydraulic press or pulling fixture may then be used to elongate nitinol wire 100 by stretching it super-elastically. Nitinol wire 100 may be stretched to the degree noted above, and prior to any breaking point of nitinol wire 100.

Figure 1A:
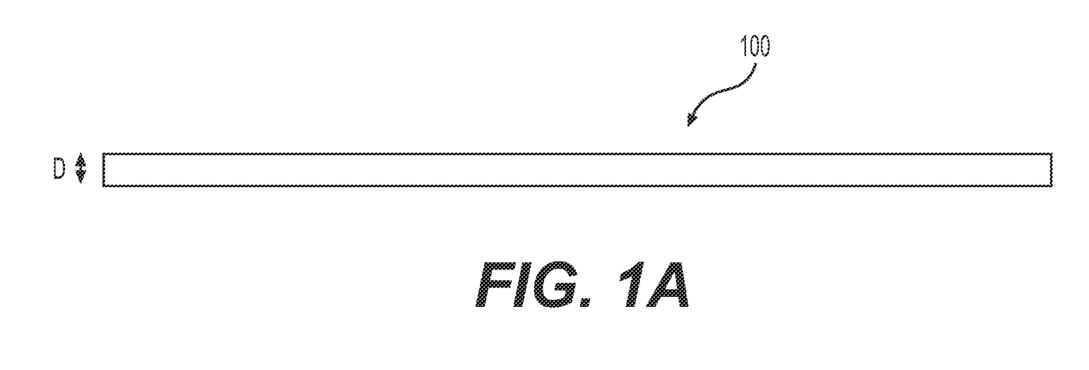
FIGS. 1A-1B are respectively a side view of an unaltered nitinol wire and a front view of a receiver, according to an embodiment.
Figure 1B:
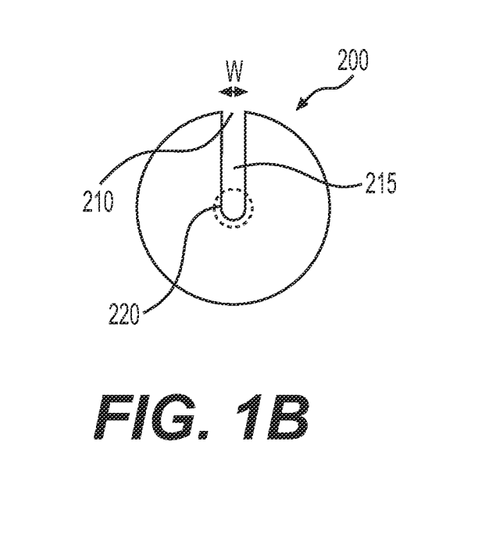
Figure 2A:
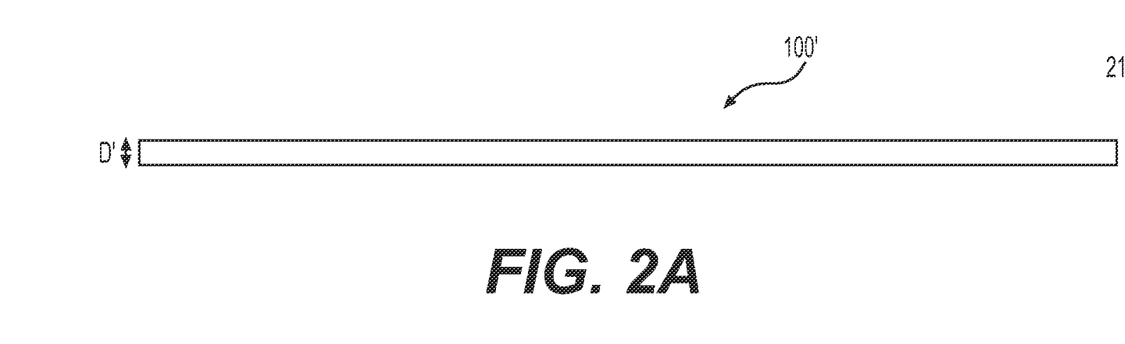
FIGS. 2A-2B are respectively a side view of the nitinol wire of FIG. 1A that has been stretched, and a front view of the receiver of FIG. 1B including the stretched nitinol wire of FIG. 2A.
Figure 2B:
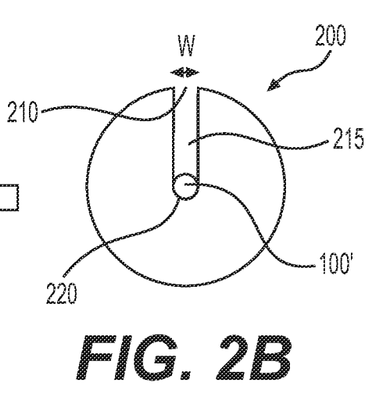
Figure 2C:
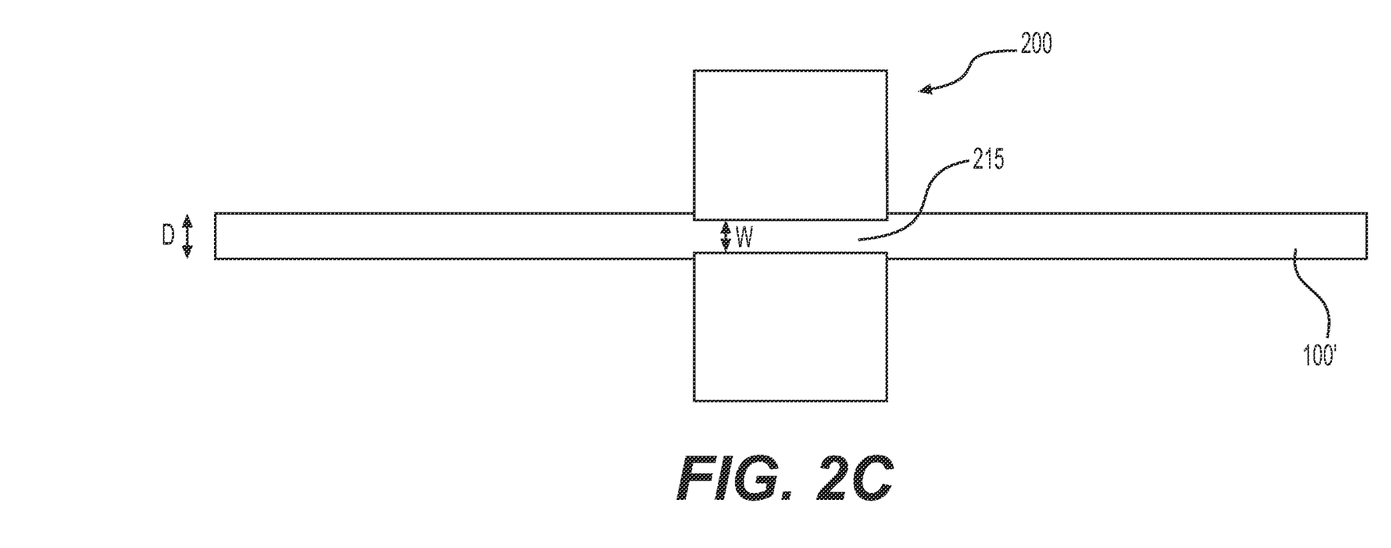
FIG. 2C is a top view of the receiver and the nitinol wire of FIG. 2B.
Figure 2D:
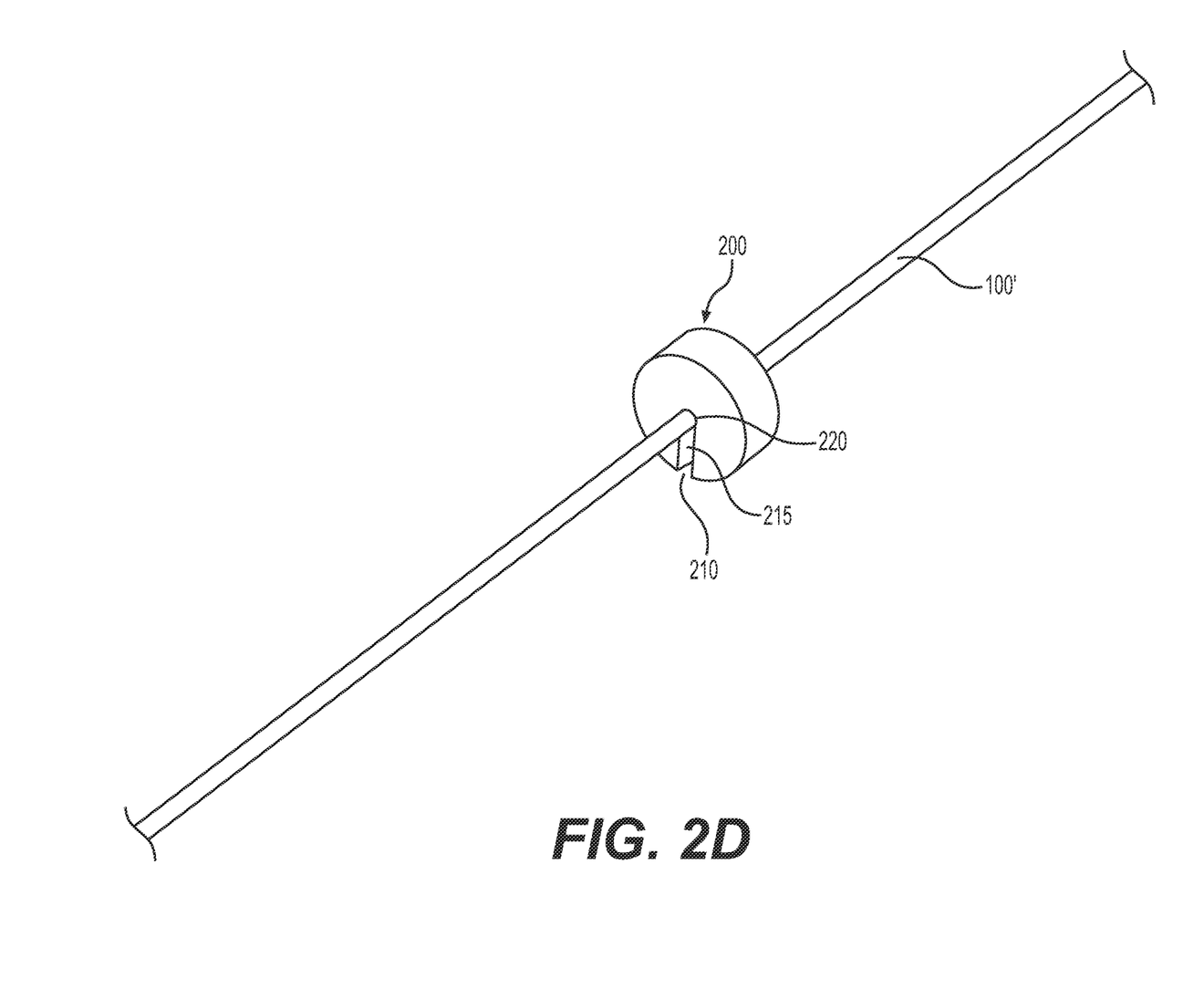
FIG. 2D is a perspective view of the receiver and the nitinol wire of FIG. 2B.

Due to stretched nitinol wire 100' having diameter D', stretched nitinol 100' may subsequently be fitted/slotted into receiver 200, via opening 210 (shown in FIGS. 2A-2B). Due to nitinol's shape recovery properties, nitinol wire 100' is fitted/slid into opening 210 and slot 215 prior to it reverting back to its original dimensions, e.g., diameter D. Thus, nitinol wire 100' may be joined to receiver 200, while maintaining diameter D'. The manner by which nitinol wire 100' is fitted onto receiver 200 is not particularly limited. For example, receiver 200 may be slid over nitinol wire 100', via opening 210, until nitinol wire 100' reaches end point 220 of slot 215. It is further noted that receiver 200 is not limited to receiving one nitinol component, e.g., a single nitinol wire, but may also be configured to receive a plurality thereof, e.g., multiple nitinol wires. For example, multiple nitinol wires may be stacked within slot 215, and/or receiver 200 may include multiple openings and slots radially arranged about receiver 200. It is noted that opening 210 of receiver 200 is not particularly limited to a slot. Opening 210 may be any suitable opening that may receive wire 100'. For example, opening 210 of receiver 200 may be a thru-hole, instead of a slot, that wire 100' may be threaded through in an elongated state.

Once nitinol wire 100' is fitted onto receiver 200, the force applied to nitinol wire 100' may be removed so that nitinol wire 100' may transition to a relaxed state. This allows portions of nitinol wire 100', not fitted within slot 215, to revert back to their original dimensions, e.g., diameter D. The portion of nitinol wire 100' fitted within slot 215 expands to a diameter corresponding to width W. For example, in instances in which diameter D' is less than width W, the portion of nitinol wire 100' fitted within slot 215 may expand to fill width W. As a result, nitinol wire 100' is securely fitted within slot 215 of receiver 200. In exemplary embodiments, receiver 200 may be coupled to nitinol wire 100' so that it is not rotatable relative to nitinol 100'. The remaining portions of nitinol wire 100' revert back to original diameter D, e.g., approximately 0.029", via its shape recovery properties. As a result, receiver 200 is inhibited from translating along the longitudinal axis of nitinol wire 100', due to the interference fit between wire 100' and receiver 200.

As disclosed above, the device component being altered and coupled to another device component is not limited to being a wire. The device component may be any suitable shape or form having a first configuration that inhibits the component from fitting into receiver 200, via opening 210, and a second configuration upon being altered so that it may fit into opening 210.

Likewise, receiver 200 is not limited to being disk-shaped, and opening 210 and slot 215 are not limited to those shown in the Figures. Receiver 200 may be of any suitable material and form/shape. Opening 210 and slot 215 may also be of any suitable width and shape, so long as it is configured to receive a device component in its second, altered configuration. In some examples, receiver 200 may include a plurality of openings and slots, having different shapes and/or dimensions. Moreover, as noted above, alteration of a device component from its first configuration to a second configuration is not limited to stretching. The device component may be altered in any suitable manner to be fitted into opening 210.

Figure 3A:
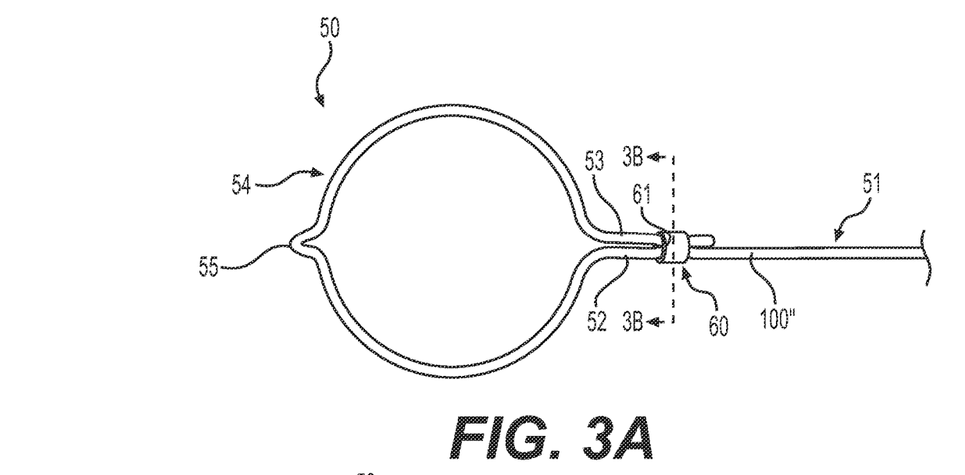
FIG. 3A is a perspective view of a medical device apparatus, according to an embodiment.

The above-described method may be used to couple device components, e.g., nitinol parts, to other medical device components, e.g., receivers, of medical apparatuses or devices. Referring to FIGS. 3A-4, examples of such medical apparatuses and devices are described below.

FIG. 3A shows a medical device 50 including a single nitinol wire 100" used for an actuation element 51 and an end effector 54. Wire 100" extends distally from another medical device component, e.g., a handle (not shown). Actuation element 51 is proximal to end effector 54. Actuation element 51 may be coupled to a handle (not shown) at a proximal end of the device in any suitable manner. Actuation element 51 and end effector 54 may translate linearly along the longitudinal axis of element 51. Both element 51 and end effector 54 may extend through a sheath of the device (not shown). The loop of end effector 54 may open and close by end effector 54 moving in and out of the sheath (not shown).

Nitinol wire 100" may be in the shape of a wire, cable, or a ribbon, and may be of any suitable cross-sectional shape or dimension, accommodating for receiver 61. The portion of wire 100" that is proximal to end effector 54, is a first strand 52 of actuation element 51. The portion of nitinol wire 100" distal to actuation element 51 defines end effector 54, e.g., the distal loop in a plane. The dimensions and the shape of end effector 54 is not particularly limited, and may be, for example, a circle, oval, teardrop, etc. The distalmost end of end effector 54 may include a tip 55. Tip 55 may be a distal protrusion, thereby forming a traumatic distal tip. However, tip 55 is not particularly limited nor necessary in end effector 54. In some other embodiments, end effector 54 may have an atraumatic distal tip.

The distal portion of nitinol wire 100" forms the loop of end effector 54 by looping back on itself. A remaining portion of wire 100" that is distal to the portion of wire 100" forming end effector 54, is straightened out to form a second strand 53. First strand 52 and second strand 53 are parallel to one another, and are both proximal to loop 54. The length of second strand 53 is not particularly limited. Strands 52 and 53 may contact one another or be spaced apart by any suitable distance, accommodating for the opening(s) of receiver 60.

Figure 3B:
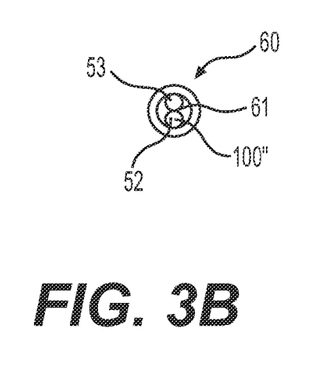
FIG. 3B is a cross-sectional view of a receiver of the apparatus of FIG. 3A, along lines 3B-3B.
Figure 4:
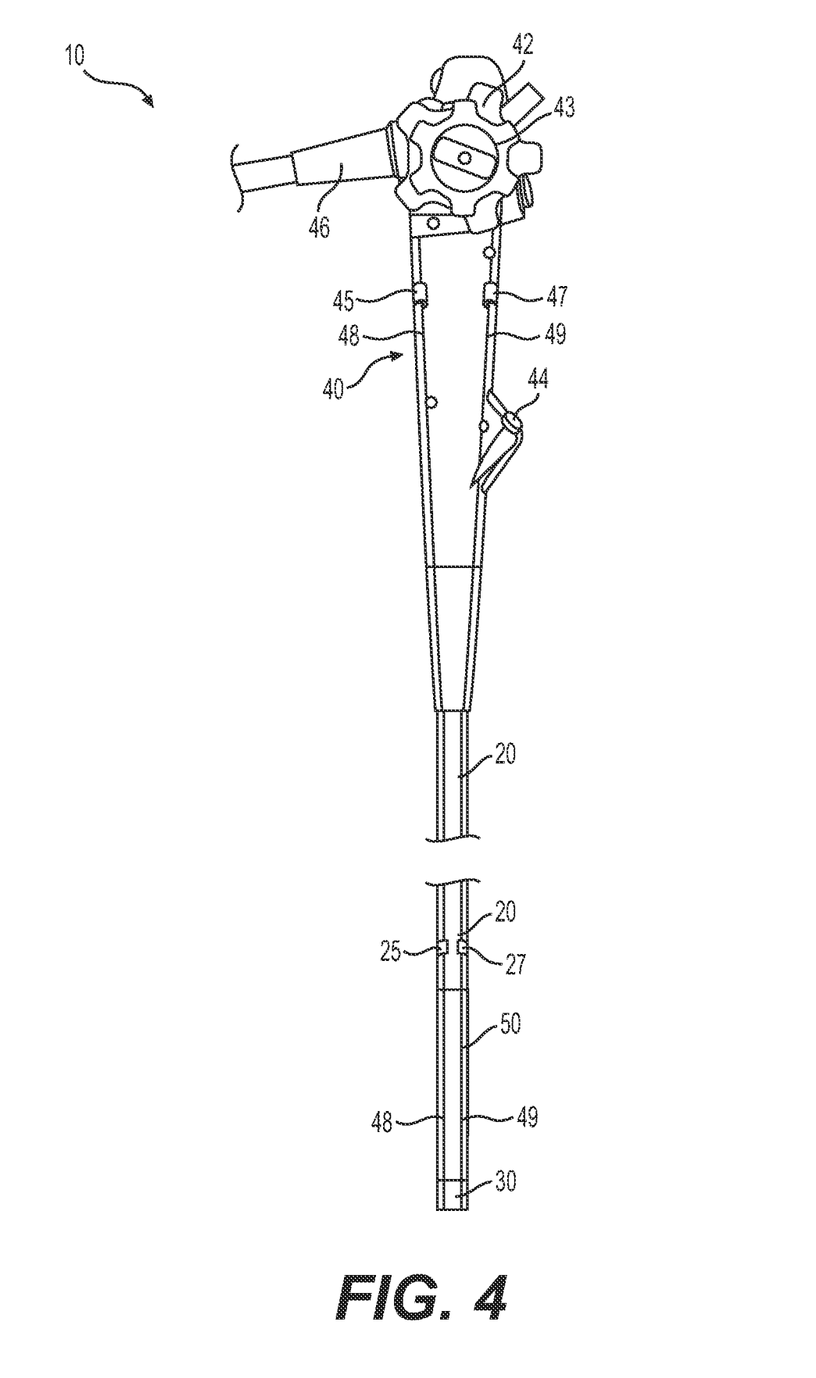
FIG. 4 is a perspective view of a medical device, according to an embodiment.

Still referring to FIGS. 3A-3B, medical device 50 further includes a receiver 60. Receiver 60 may be of any suitable material, e.g., stainless steel. Receiver 60 is an annular/ring component, including an opening 61. However, receiver 60 is not particularly limited to being a ring, and as discussed above, may be any suitable shape and/or dimension. Receiver 60 is a complete, closed ring. In other exemplary embodiments, however, receiver 60 may be a partial ring including a break in its annular structure. The break may be of any suitable distance that allows for receiver 60 to receive and hold strands 52 and 53. Opening 61 may be of any suitable shape, e.g., circular, rectangular, and may be a shape accommodating for the cross-sectional shape of strands 52 and 53. Opening 61 should have a width or diameter that is less than the combined diameters of strands 52 and 53, but is not particularly limited. In other exemplary embodiments, receiver 60 may have two separate openings, each for a corresponding strand 52 and 53. In such embodiments, both openings may have diameters less than each of the diameters of strands 52 and 53.

Strands 52 and 53 of nitinol wire 100" are coupled to receiver 60, via the coupling method described above. Strands 52 and 53, in their unaltered state, e.g., a first configuration, have a combined width/diameter that is larger than the width/diameter of opening 61. Strands 52 and 53 are altered into a second configuration, e.g., stretched/thinned, to be coupled to receiver 60. As shown in FIG. 3B, strands 52 and 53 are thinned so that they fit within opening 61. In some examples, strands 52 and 53 may have been stretched and inserted into opening 61 sequentially or simultaneously. In other examples, nitinol wire 100" may have been stretched prior to forming distal loop 54, so that strands 52 and 53 were already in a thinned/stretched state when coupled to receiver 61. Regardless of the manner in which it is done, alteration into a second configuration may involve a reduction of the cross-sectional dimension of a device component, e.g., strands 52 and 53.

After thinning strands 52 and 53, receiver 60 is fitted over thinned strands 52 and 53 (or thinned nitinol wire 100" prior to forming loop 54), via opening 61. The manner in which receiver 60 is fitted over strands 52 and 53 is not particularly limited. In some examples, receiver 60 is fitted over thinned strands 52 and 53 prior to actuation element 51 being coupled to another device component, e.g. a handle (not shown). In other examples, receiver 60 is fitted over thinned nitinol wire 100", prior to forming the loop of end effector 54. Subsequently, the looped-back portion of nitinol wire 100" (forming second strand 53) may be slid through opening 61, while or after forming end effector 54. In other exemplary embodiments when receiver 60 is a partial ring, receiver 60 may be slid onto thinned strands 52 and 53, via the break in the partial ring. Receiver 60 may be fitted over strands 52 and 53 in various other manners, beyond the examples described above.

After fitting receiver 60 over strands 52 and 53, the force applied to strands 52 and 53 may be removed so that strands 52 and 53 may transition to a relaxed state. This allows portions of strands 52 and 53 fitted within opening 61 to expand to the extent allowed by opening 61. However, the fitted portions of strands 52 and 53 are not expanded to their original diameters due to the spatial constraints of opening 61. Meanwhile, the remaining portions of strands 52 and 53, not fitted within opening 61, revert back to their original dimensions, e.g., diameters, due to the shape recovery properties of nitinol wire 100". Thus, receiver 60 may be inhibited from translating along the longitudinal axes of strands 52 and 53, due to the interference fit between strands 52 and 53, and receiver 200.

Figure 3C:
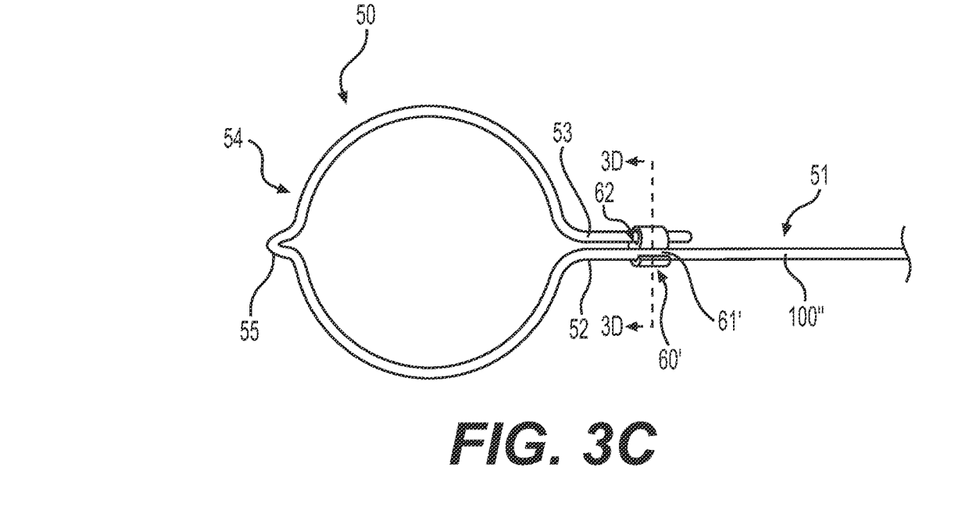
FIG. 3C is a perspective view of a medical device apparatus, according to another embodiment.
Figure 3D:
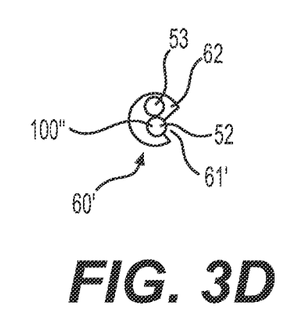
FIG. 3D is a cross-sectional view of a receiver of the apparatus of FIG. 3C, along lines 3D-3D.

FIGS. 3C-3D show a device similar to the one shown in FIGS. 3A-3B, except receiver 60' differs from receiver 60. Receiver 60' includes two openings 61' and 62. Openings 61' and 62 are configured to receive first and second strands 52 and 53, respectively. Thus, opening 61' may be positioned directly below opening 62. Openings 61' and 62 may be spaced apart in accordance with the distance between strands 52 and 53. Opening 61' is a clamp-like opening that receives first strand 52. Opening 61' may be any suitable shape that accommodates for first strand 52. Opening 61' may also be any suitable width that is less than or equal to the width/diameter of first strand 52 when unaltered. Opening 62 receives second strand 53. Opening 62 is within the structure of receiver 60, and extends longitudinally. Thus, unlike opening 61', opening 62 is a fully enclosed opening. Opening 62 may be any suitable shape that accommodates for second strand 53. Opening 62 may also be any suitable width/diameter that is less than the width/diameter of second strand 53 when unaltered.

Strands 52 and 53 of nitinol wire 100" are also coupled to receiver 60', via the coupling method described above. For example, second strand 53 is altered, e.g., stretched/thinned, so that receiver 60' may be slid onto second strand 53, via opening 62. Receiver 60' is fitted onto any portion of second strand 53, so long as it is proximal to distal loop 54. In some examples, in which the width of opening 61' is less than the width/diameter of first strand 52, first strand 52 is also altered, e.g., stretched/thinned, so that strand 52 may be fitted into clamp-like opening 61'. In other examples, in which the width of opening 61' is equal to or about equal to the width/diameter of first strand 52, unaltered first strand 52 is fitted into clamp-like opening 61' via any suitable manner.

FIG. 4 shows an example of a medical device, e.g., an endoscope, including nitinol parts coupled to other medical device components, e.g., receivers, via the method described above. Endoscope 10 includes a flexible shaft 20, a tip 30 at a distal end of endoscope 10, and an articulation joint 50 disposed between and connecting flexible shaft 20 and tip 30. A handle 40 or some other device for actuating or controlling endoscope 10, and any tool or devices associated with endoscope 10, is connected at a proximal end of flexible shaft 20.

A plurality of actuating elements, such as nitinol steering wires 48 and 49 suitable for medical procedures, may extend distally from handle 40. Wires 48 and 49 may be supported and secured by medical device components, e.g., a plurality of receivers 45, 47, 25, and 27, via the coupling method described above. Thus, wires 48 and 49 may be securely fitted onto receivers 45, 47, 25, and 27, via an interference fit between the wires and the receivers. Proximal receivers 45 and 47 are positioned at a suitable location within handle 40. The manner by which receivers 45 and 47 are positioned, e.g., molded, adhered, etc., is not particularly limited. Receivers 45 and 47 may be any of the above described receivers, or variations thereof. Distal receivers 25 and 27 are positioned within shaft 20. Additionally, or alternatively, distal receivers 25 and 27 may be positioned anywhere suitable within tip 30 or an articulating joint 50. The manner by which receivers 25 and 27 are positioned, e.g., molded, adhered, etc., is not particularly limited. Receivers 25 and 27 may also be any of the above described receivers, or variations thereof.

Nitinol wires 48 and 49 may be indirectly coupled to first and second actuating devices 42, 43, which control articulation of articulation joint 50 in multiple directions. Devices 42, 43, may be, for example, rotatable knobs that rotate about their axes to push/pull nitinol steering wires 48 and 49.

Alternatively, or additionally, a user may operate steering wires 48, 49 independently of handle 40. Distal ends of steering wires 48, 49 extend through flexible shaft 20 and terminate at articulation joint 50 and/or tip 30. For example, one or more steering wires 48, 49 may be connected to articulation joint 50 and one or more other steering wires 48, 49 may be attached to tip 30. Actuation of steering wires 48, 49 may control articulation joint 50, tip 30, and/or elements attached to tip 30, such as an end effector (not shown). In addition, one or more electrical cables (not shown) may extend from the proximal end of endoscope 10 to tip 30 and may provide electrical controls to imaging, lighting, and/or other electrical devices on tip 30, and may carry imaging signals from tip 30 proximally to be processed and/or displayed on a display. Handle 40 may also include ports 44, 46 for introducing and/or removing tools, fluids, or other materials from the patient. Port 44 may be used to introduce tools. Port 46 may be connected to an umbilicus for introducing fluid suction, and/or wiring for electronic components.

It will be apparent to those skilled in the art that various modifications and variations can be made to the disclosed stapling mechanism without departing from the scope of the disclosure. For examples, the configuration of a coupler, actuator, and a stapler may be altered to suit any medical device, and are not limited to the examples described herein. Other embodiments of the disclosure will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A medical device comprising:
a nitinol wire defining a loop, a first strand, and a second strand, each of the first strand and the second strand extending proximal to the loop; and
a receiving component coupled to the first strand and the second strand, wherein the receiving component includes a first opening, and a portion of the first strand extends through the first opening, wherein a diameter of the portion of the first strand is less than a diameter of a remaining portion of the first strand, wherein a portion of the second strand extends through the first opening, wherein a diameter of the portion of the second strand is less than a diameter of the remaining portion of the second strand.

2. The medical device of claim 1, wherein a diameter of the first opening is less than a combined diameter of the portion of the first strand and the portion of the second strand.

3. The medical device of claim 2, wherein the first strand and the second strand contact one another within the receiving component.

4. The medical device of claim 2, wherein the first strand and the second strand are spaced apart from one another within the receiving component.

5. The medical device of claim 1, wherein the receiving component includes a second opening and a portion of the second strand extends through the second opening, wherein a diameter of the portion of the second strand is less than a diameter of a remaining portion of the second strand.

6. The medical device of claim 5, wherein the receiving component is a partial ring.

7. The medical device of claim 1, wherein a diameter of the portion of the first strand is less than a diameter of a portion of the nitinol wire defining the loop.

8. The medical device of claim 1, wherein the receiving component is slidable along the first strand when the first strand is in an altered state.

9. The medical device of claim 8, wherein the receiving component is fixed along the first strand when the first strand is in a natural state.

10. A medical device comprising:
a nitinol wire defining a loop, a first strand, and a second strand, each of the first strand and the second strand extending proximal to the loop; and
a receiving component comprising a partial ring coupled to the first strand and the second strand, wherein the receiving component includes a first opening and a second opening, a portion of the first strand extends through the first opening, and a portion of the second strand extends through the second opening,
wherein a diameter of the portion of the first strand is less than a diameter of a remaining portion of the first strand,
wherein a diameter of the portion of the second strand is less than a diameter of a remaining portion of the second strand,
wherein a diameter of the portion of the first strand is less than a diameter of a portion of the nitinol wire defining the loop,
wherein a diameter of the portion of the second strand is less than the diameter of the portion of the nitinol wire defining the loop,
wherein the first strand and the second strand are parallel to each other outside the partial ring and contact one another within the partial ring.

11. The medical device of claim 10, wherein the first strand and the second strand are spaced apart from one another within the partial ring.

12. The medical device of claim 10, wherein a combined diameter of the portion of the first strand and the portion of the second strand is less than a combined diameter of the first opening and the second opening.

13. The medical device of claim 10, wherein the partial ring is slidable along the first strand when the first strand is in an altered state, and wherein the partial ring is fixed along the first strand when the first strand is in a natural state.

14. A medical device comprising:
a nitinol wire defining a loop, a first strand, and a second strand, each of the first strand and the second strand extending proximal to the loop; and
a receiving component coupled to the first strand and the second strand, wherein the receiving component includes a first opening and a second opening, a portion of the first strand extends through the first opening, and a portion of the second strand extends through the first opening,
wherein a diameter of the portion of the first strand is less than a diameter of a remaining portion of the first strand,
wherein a diameter of the portion of the second strand is less than a diameter of a remaining portion of the second strand,
wherein the receiving component is slidable along the first strand when the first strand is in an altered state and the receiving component is fixed along the first strand when the first strand is in a natural state, and
wherein the receiving component includes a closed ring, a partial ring, or a disk-shaped receiver.

15. The medical device of claim 14, wherein the receiving component is slidable along the second strand when the second strand is in an altered state, wherein the receiving component is fixed along the second strand when the second strand is in a natural state.

* * * * *